US006911535B2

(12) United States Patent
Schwartz

(10) Patent No.: US 6,911,535 B2
(45) Date of Patent: Jun. 28, 2005

(54) BIOMOLECULE/POLYMER CONJUGATES

(75) Inventor: David A. Schwartz, Encinitas, CA (US)

(73) Assignee: Solvlink Biosciences, San Diego, CA (US)

( * ) Notice: Subject to any disclaimer, the term of this patent is extended or adjusted under 35 U.S.C. 154(b) by 75 days.

(21) Appl. No.: 10/050,277

(22) Filed: Jan. 15, 2002

(65) Prior Publication Data

US 2002/0146504 A1 Oct. 10, 2002

(51) Int. Cl.[7] .................. C07K 1/00; C07K 17/00; C08H 1/00; C12N 11/08; C07H 21/00
(52) U.S. Cl. ............... 530/402; 435/180; 530/395; 530/815; 530/816; 536/22.1
(58) Field of Search .................. 530/402, 815, 530/816, 395; 435/180, 181; 536/22.1

(56) References Cited

U.S. PATENT DOCUMENTS

| | | | | |
|---|---|---|---|---|
| 4,801,688 A | * | 1/1989 | Laguzza et al. | 530/391 |
| 5,262,317 A | * | 11/1993 | Howard, Jr. et al. | 435/180 |
| 5,276,013 A | * | 1/1994 | Conrad et al. | 514/2 |
| 5,541,307 A | * | 7/1996 | Cook et al. | 536/23.1 |
| 5,783,682 A | * | 7/1998 | Cook et al. | 536/24.3 |
| 5,981,734 A | * | 11/1999 | Mirzabekov et al. | 536/25.3 |
| 6,013,789 A | * | 1/2000 | Rampal | 536/25.3 |
| 6,114,509 A | * | 9/2000 | Olsen et al. | 530/402 |
| 6,133,436 A | * | 10/2000 | Koster et al. | 536/24.3 |
| 6,566,055 B1 | * | 5/2003 | Monforte et al. | 435/6 |

* cited by examiner

*Primary Examiner*—David M. Naff
(74) *Attorney, Agent, or Firm*—David B. Waller & Assoc.

(57) ABSTRACT

The present invention is directed to methods for immobilizing natural or synthetic biomolecules to surfaces. The methods comprise covalently linking the natural or synthetic biomolecule to a mono- or bi-functional polymer and covalently and/or electrostatically immobilizing the biomolecule/polymer conjugate to an unmodified or modified surface. The biomolecule is an oligonucleotide, a polynucleotide, a protein, a glycoprotein, a peptide or a carbohydrate that has been modified to incorporate a single or plurality of nucleophilic groups. These groups comprise an aliphatic or aromatic amino, thiol, hydrazine, thiosemicarbazide, hydrazide, thiocarbazide, carbazide, aminooxy, a derivative of 2-hydrazinopyridine or aminoxyacetic acid or a single or plurality of electrophilic groups. The electrophilic groups comprise an aliphatic or aromatic aldehyde, ketone, epoxide, isocyanate, isothiocyanate, succinimidyl ester or cyanuric chloride or a linkable aromatic aldehyde or ketone. The surface has been modified to possess either neutral, cationic or anionic groups or a combination neutral, anionic and/or cationic moieties.

2 Claims, 7 Drawing Sheets

Figure 1
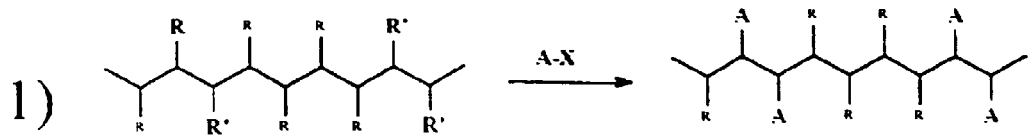
where R' is the same or different than R
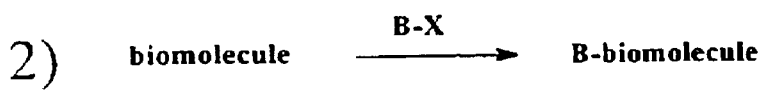
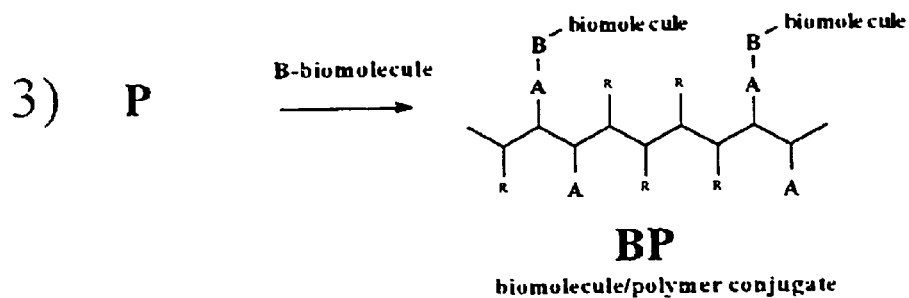
BP
biomolecule/polymer conjugate
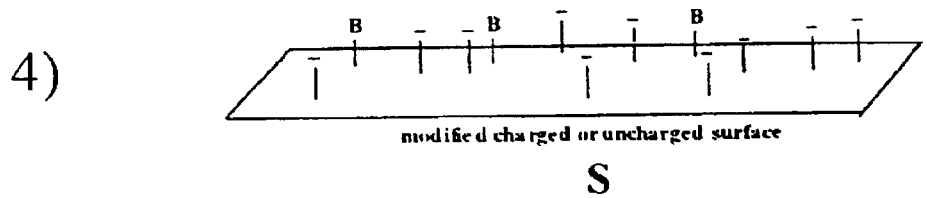
modified charged or uncharged surface
S
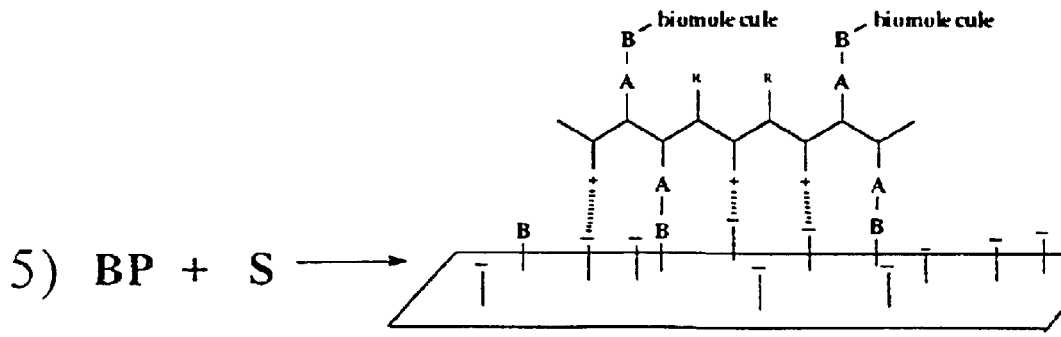
BPS
biopolymer/polymer/surface ternary system Figure 3
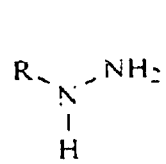
hydrazine
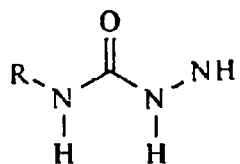
semicarbazide
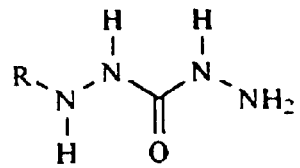
carbazide
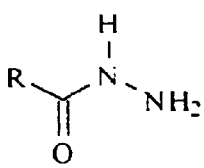
hydrazide
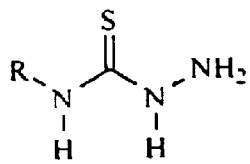
thiosemicarbazide
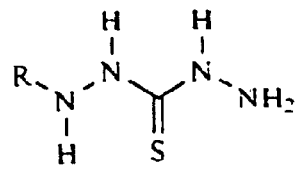
thiocarbazide
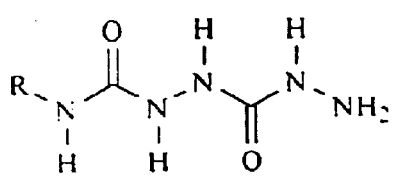
carbonic acid dihydrazine
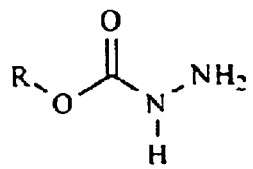
hydrazine carboxylate
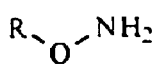
aminooxy
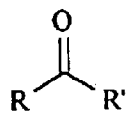
R = alkyl, aromatic or heteroaromatic group
R' = H or straight, branched or cyclic alkyl moiety or aromatic or heteroaromatic moiety
carbonyl derivatives

Figure 5

A. H2N-oligo
B. OHCΦ-oligo
C. H2NHN-oligo
D. H2NHNCO-olig

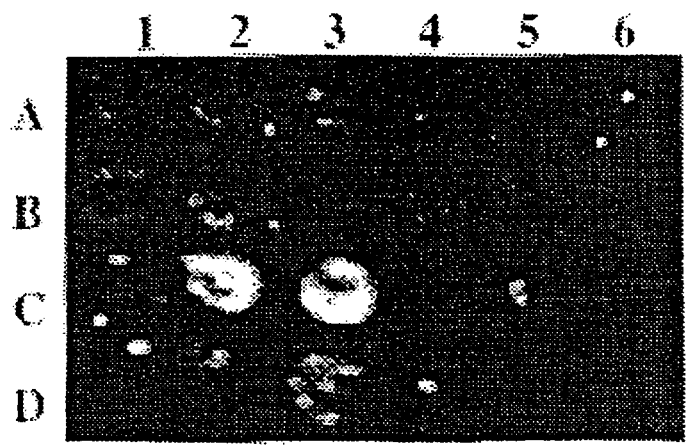

1) polyK (20K MW)
2) polyK/ΦCHO (10X)
3) polyK/ΦCHO (20X)
4) polyK/HyNic (10X)
5) polyK/HyNic (20X)
6) no polymer Figure X: Matrix experiment (see Example 2) demonstrating the covalent nature of the immobilization of a 5'-hydrazino oligo//sCHO/poly-l-lysine (polyK) conjugate on a amino modified glass slide following hybridization to its fluorescent complement.

A. H2N-oligo
B. OHC-oligo
C. H2NHN-oligo
D. H2NHNCO-oligo 1) polyK (20K MW)
2) polyK/sCHO (10X)
3) polyK/sCHO (20X)
4) polyK/HyNic (10X)
5) polyK/HyNic (20X)
6) no polymer

BIOMOLECULE/POLYMER CONJUGATES

RELATED APPLICATIONS

This application is related to co-owned U.S. utility application entitled "TRIPHOSPHATE OLIGONUCLEOTIDE MODIFICATION REAGENTS AND USES THEREOF", to Schwartz et al., filed Aug. 1, 2000, patent application Ser. No.: 09/630,627, now U.S. Pat. No. 6,686,461 B1. This application is related to co-owned U.S. utility application, entitled "FUNCTIONAL BIOPOLYMER MODIFICATION REAGENTS AND USES THEREOF", to Schwartz et al., filed Aug. 1, 2000, patent application Ser. No.: 09/630,060 and to patent application Ser. No. 09/815,978, entitled "HYDRAZINE-BASED AND CARBONYL-BASED BIFUNCTIONAL CROSSLINKING REAGENTS", to Schwartz, filed Mar. 22, 2001, now U.S. Provisional Application Ser. No. 60/191,186 filed Mar. 22, 2000. The above-referenced applications are incorporated herein by reference in their entirety.

BACKGROUND OF THE INVENTION

Proteomic and genomic microarray technology allows researchers to perform multiple experiments simultaneously, "multiplexing", as hundreds to thousands of proteins or genes are immobilized on a surface and exposed to target ligands to determine the proclivity of the immobilized protein for its ligand or for an oligonucleotide to hybridize to its complement in competition with other targets. The production of both protein and poly/oligonucleotide microarrays is currently very inefficient due to the sub-optimal properties of bioconjugation methods available to immobilize protein and poly/oligonucleotides. This invention describes novel, efficient and simple methods for immobilization of oligonucleotides, proteins and other biomolecules to surfaces.

Poly/oligonucleotide immobilization: There are two technologies being employed to produce oligonucleotide microarrays (see page 6, DNA Microarrays, M. Schena, Oxford University Press. Oxford, England OX2 6DP). One is direct synthesis of oligonucleotides on surfaces via photolithography (www.affymetrix.com, Affymetrix, Inc., Sunnyvale, Calif.) or use of reagent-directed devices such as inkjet spotters. A second method is covalent attachment of an oligonucleotide modified to possess a reactive functionality bonding to its reactive partner that has been immobilized on the surface.

The direct synthesis method allows for very dense microarrays, i.e. up to 250K oligos/sq. centimeter on a slide. This method however has significant shortcomings in that failure sequences remain on the chip, yields of each coupling step is low, ~95%, leading to both poor yield of full length product and the inability to produce oligonucleotides longer than 20–25 mers. The presence of failure sequences could also lead to false positive hybridization results. Also due to the length of the sequence immobilized on the surface, <25 mers, multiple sequences to each gene must be immobilized on the surface to overcome the inherent wide difference in Tm, melting temperatures, of 25 mers. Sequences must be designed carefully and a deconvoluting step is required in the analysis of the results.

Covalent attachment methods also have limitations due to poor stability of surface chemistry immobilization of the first reaction partner also due to the small spotting volumes, ~1 nL, there is fast drying of the spot which does not allow sufficient time for covalent chemistry to occur. Poor water stability of one or both of the reactive components of the bioconjugation couples such as maleimido/thiol, succinimidyl ester/amino will also significantly reduce the efficiency of coupling.

Preparation of PCR- and cDNA-based arrays is routinely accomplished by electrostatic immobilization of the anionic polynucleotide to a surface that has been modified to incorporate cationic species. The two major cationic-based slides are produced from aminopropylsilane or cationic polymers such as poly-1-lysine or polyethyleneimine. While arrays produced by electrostatic immobilization on cationic surface gives a product that has yielded good results, the immobilization efficiency of the polynucleotides is poor <20%. This poor yield is of importance due to the cost of producing PCR or cDNA products. Also the reproducibility of slides is capricious.

The optimal polynucleotide microarray for gene expression analysis would be an oligonucleotide-based microarray consisting of oligonucleotides of 60–80 mer oligonucleotides immobilized on surfaces. This type of array would be preferred over cDNA arrays as the cost of producing 60–80 mer oligonucleotides would be far cheaper, more easily reproducible, automatable and oligonucleotides can be more easily scaled up to produce larger- almost unlimited- quantities of product. The optimal length of oligonucleotides for SNP (single nucleotide polymorphism) analysis on microarrays is 20–25 oligonucleotides while oligonucleotides of 60–80 bases are preferred for gene expression analysis.

The power of the microarray is the massive number of experiments that can be performed simultaneously in a small area requiring minimal amounts of reagents and samples. However to prepare 10–100 $\mu m^2$ spots incorporating the biomolecule small volumes (<10 nL) are spotted. These small volumes evaporate too quickly and therefore reaction time for covalent chemistry to occur between the biomolecule and the surface is insufficient leading to extremely poor yields and poor reproducibility. Devices to retain humidity during spotting have been developed but do not solve the evaporation problem completely.

In the case of direct oligonucleotide immobilization there is single point attachment between the oligonucleotide and the surface. The reaction kinetics in a two-phase system is slower than solution phase kinetics. The formation of a covalent bond in water is slow as well as the competing hydrolysis of the electrophilic partner in the reaction. The competing electrostatic interaction between the oligonucleotide and a glass surface will also interfere with the covalent chemistry.

Protein Immobilization: Current methods to immobilize proteins to surface include direct binding of proteins to poly-cationic glass surfaces (B. B. Haab, M. J. Dunham and P. O. Brown, Genome Biol. 1, (2000)). This method functioned well for immobilization of families of proteins such as antibodies but when different proteins or antigens were immobilized the binding was not as efficient or consistent.

Macbeath and Schreiber (Science 289, 1760 (2000)) also describe direct immobilization of protein on modified surfaces. They directly immobilized proteins on aldehyde coated glass surfaces via multiple imine bonds. They also describe pre-coating glass slides with bovine serum albumin (BSA) and subsequently reacting the amino groups on the protein with homo-bifunctional succinimidyl esters. The succinimidyl groups on the protein are subsequently used to react with amino groups on the desired protein to form an immobilized conjugate.

Thus, due to the limitations of currently available methods as described above, there is a need for efficient methods for producing both protein and poly/oligonucleotide-based microarrays. Therefore, it is an object herein to provide ternary systems based on both novel bifunctional polymers and biomolecule/bifunctional polymer conjugates and methods to immobilize these conjugates on modified and unmodified surfaces for the efficient and reproducible production of both polynucleotide and oligonucleotide-based microarrays.

SUMMARY OF THE INVENTION

Ternary systems B/P/S comprised of biomolecule (B)/polymer (P) conjugates, B/P, linked electrostatically and/or covalently to modified and unmodified surfaces (S) to produce biomolecule microarrays are provided. Methods to produce both polynucleotide and oligonucleotide arrays as well as protein and peptide arrays are given. The general scheme for these systems is schematically represented in FIG. 1.

The first component of the ternary B/P/S is a biomolecule modified with a reactive moiety that does not interfere with the function of the biomolecule. The second component is a polymer modified with a reactive moiety that reacts with the reactive moiety on the biomolecule to form a covalent linkage. The polymer may also possess a third type of reactive moiety that does not react with the reactive moiety on the biomolecule. The third component is a solid surface such as silica-based surfaces, i.e. glass, silica beads or fibre optic bundles. Other third component solids surfaces include plastic, latex beads, membranes such as cellulose or nitrocellulose or metal such as gold that is unmodified or modified with the same reactive moiety as incorporated on the biomolecule. The surface may also possess a reactive moiety that forms a covalent linkage with the second reactive component on the polymer.

The optimal bioconjugation reaction chemistry for enablement of this invention comprises use of reactive moieties following incorporation onto any of the components are stable and form stable covalent linkages with good kinetics. This invention provides such chemistries and methods.

A major advantage of the ternary BPS systems is that covalent attachment of the biomolecule to the polymer occurs in solution without reaction time limitations. In contrast to direct single point attachment of the biomolecule to the surface this method provides multiple point covalent attachment points between the modified polymer and the surface as well as electrostatic interactions. This method produces higher yielding more stable immobilzation and better reproducibility than the previous described methods.

Charged and uncharged polymers modified to incorporate reactive functionalities are provided for covalent attachment of biomolecules, especially poly/oligonucleotides and peptides/proteins. Methods to conjugate these biomolecules to the polymers are provided as well as methods for electrostatic and/or covalent attachment to modified and unmodified surfaces are provided.

The most direct, simple and efficient preparation of an oligonucleotide/polymer conjugate would have the following properties: (1) direct incorporation of the first reactive component of the bioconjugate couple directly on the oligonucleotide or peptide during solid phase synthesis without the requirement for any post-synthetic activation, (2) indefinite stability of both reactive components of the bioconjugate couple following incorporation on either the biomolecule or the polymer, (3) good kinetics of covalent bond formation between the modified oligonucleotide and the modified polymer without the need for a reagent-mediated reaction or competing reactions on the bioconjugate couple moieties such as hydrolysis, (4) simple incorporation of the first reactive component of the bioconjugate couple on the surface of choice, (5) fast kinetic of immobilization of the biomolecule/polymer conjugate on the modified surface, (6) long term stability of the biomolecule/polymer conjugate on the surface.

One enablement of this invention describes and demonstrates the immobilization of oligonucleotide/polymer conjugates to modified and unmodified glass surfaces in a more efficient manner than current direct spotting of modified oligonucleotides on modified surfaces.

The oligonucleotide is modified to incorporate the first reactive component of a bioconjugate couple on the 3' or 5' end of the oligonucleotide. Alternatively the first reactive component can be incorporated on any internal position of the oligonucleotides. Internal positions include but are not limited to a position on the base of the oligonucleotide such as the 5 position of a pyrimidine or on the 2' position on the sugar. A polymer is modified to incorporate the second reactive component of the bioconjugate couple. Subsequently the modified biomolecule is reacted with the modified polymer to form the desired biomolecule/polymer conjugate.

A preferred enablement of this invention requires incorporation of the first reactive component of the bioconjugate couple or a reactive moiety with similar reactivity on the surface. For example if the first reactive component is an electrophile any electrophilic reactive moiety may be incorporated on the surface that forms a covalent bond with the second reactive component on the polymer. A further preferred embodiment is immobilization of the oligonucleotide/polymer conjugate on a silica-based surface. The most preferred silica-based surfaces are glass, fiber optic wires and silica-based beads. Therefore incorporation of the first reactive component of the bioconjugate couple or a reactive component of similar reactivity on the surface is required.

The preferred bioconjugate couple to be employed in the enablement of the ternary oligonucleotide/polymer/surface system is the hydrazine/carbonyl or aminooxy/carbonyl couple (see FIG. 2). Oligonucleotide monomers containing hydrazino, oxyamino, or carbonyl groups that can be incorporated into an oligonucleotide chain during solid phase oligonucleotide synthesis are provided. Methods for immobilization and conjugation of biopolymer first components, particularly oligonucleotides, containing hydrazino, oxyamino, or carbonyl modifications are provided. The resulting first reactive components can then be used for any purpose for which oligonucleotides are used. They are particularly suitable for conjugation to a second reactive component for immobilization on a surface. The monomers provided herein are readily incorporated into oligonucleotide chains, hence can be used in any application that involves or uses an oliogonucleotide Ternary B/P/S systems wherein the biopolymer is a polynucleotide can also be prepared in a variety of ways as described in the Detailed Description section. In short, a single or a plurality of functional moieties can be incorporated either terminally or internally on the polynucleotide. The modified polynucleotide is conjugated to a polymer modified to incorporate the second reactive component of a bioconjugation couple and the polynucleotide/polymer conjugate is immobilized on a surface in an identical manner described above for oligonucleotides.

Also described are methods for preparing protein/polymer/surface and peptide/polymer/surface ternary systems. For proteins and peptides one component of a bioconjugate couple is incorporated on the protein or peptide and conjugated to a polymer modified to incorporate the second component of a bioconjugate couple. The conjugate is immobilized on a surface in an identical manner described for oligonucleotides wherein the conjugate is reacted on a surface possessing a functional group that forms a covalent and/or electrophilic bond to the reactive moiety on the polymer.

DESCRIPTION OF THE FIGURES

FIG. 1: General scheme outlining the protocol to prepare a BPS system.

FIG. 3: Structures of the hydrazine, aminooxy and carbonyl moieties that are suitable for use as partners in the hydrazine (aminooxyl/carbonyl bioconjugation couple.

FIG. 5: Matrix experiment (see Example 1) demonstrating the covalent nature of the immobilization of a 5'-aldehyde oligo//HyNic/poly-l-lysine (polyK) conjugate on an aldehyde modified glass slide following hybidization to its fluorescent complement.

DETAILED DESCRIPTION OF PREFERRED EMBODIMENTS

Definitions

Figure 2:
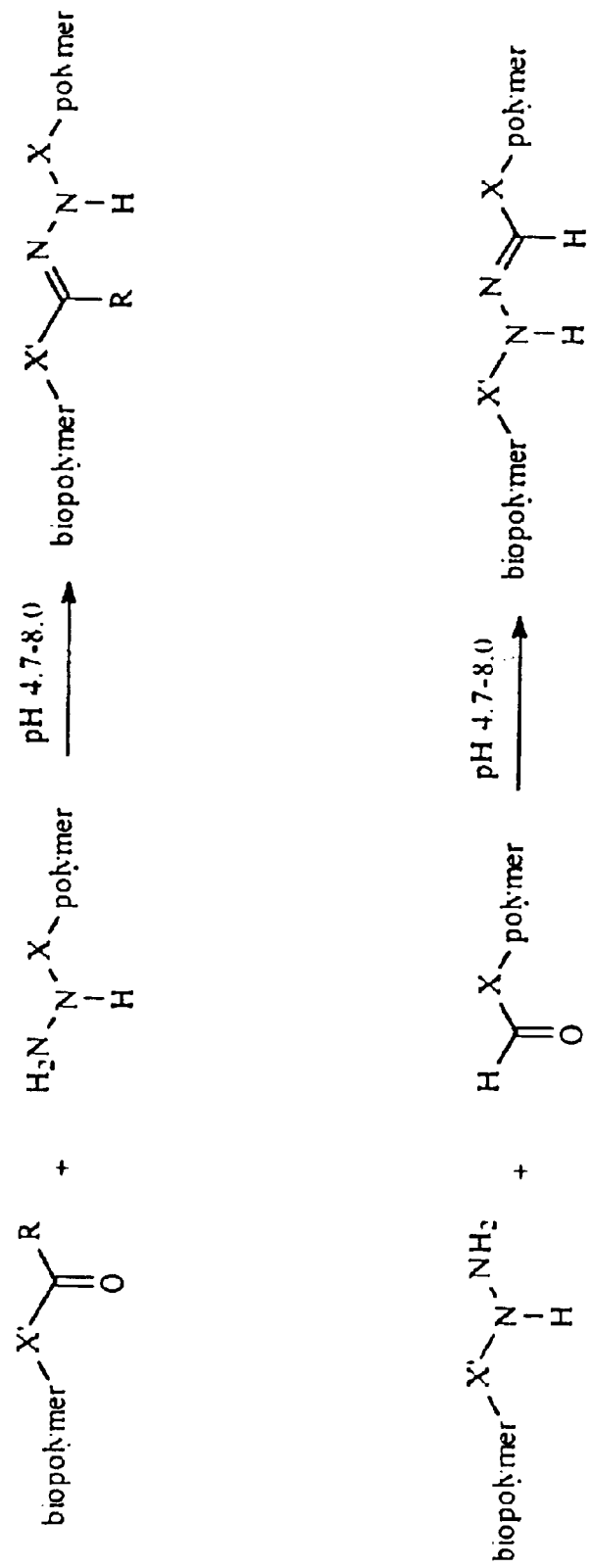
FIG. 2: Generic hydrazine (aminooxyl/carbonyl bioconjugation couple that is described for the preparation of BPS system.

Unless defined otherwise, all technical and scientific terms used herein have the same meaning as is commonly understood by one of skill in the art to which this invention belongs. All patents, patent applications and publications referred to throughout the disclosure herein are incorporated by reference in their entirety. In the event that there are a plurality of definitions for a term herein, those in this section prevail.

Polynucleotide is defined as DNA or RNA>50 bases derived from natural sources, PCR or reverse transcriptase methods Oligonucleotides are defined as any combination or DNA, RNA or PNA (peptide nucleic acids) sequences<100 bases synthesized via standard solid phase oligonucleotide methods incorporating natural or unnatural bases and natural or unnatural sugars.

A "probe" is the immobilized biomolecule such as nucleic acid with known sequence or protein or peptide or carbohydrate.

A "target" is the free biomolecule/sample whose identity/abundance is being detected.

As used herein polymers include, but are not limited to natural and synthetic polymers. As used herein polymers can be derived from biological monomers such as amino acids, nucleotides or carbohydrates or any combination thereof. As used herein polymers may be neutral, cationic or anionic or any combination thereof.

As used herein synthetic polymers may be modified to incorporate reactive moieties used in bioconjugate chemistry.

As used herein bioconjugate couples include, but are not limited to maleimido/thiol, a-bromoacetamido/thiol, succinimidyl ester/amino, avidin/biotin, hydrazine/carbonyl and pyridyldisulfide/thiol.

As used herein, "hydrazino groups" include, but are not limited to, hydrazines, hydrazides, semicarbazides, carbazides, thiosemicarbazides, thiocarbazides, hydrazine carboxylates and carbonic acid hydrazines (see, e.g., FIG. 1).

As used herein, hydrazone linkages include, but are not limited to, hydrazones, acyl hydrazones, semicarbazones, carbazones, thiosemicarbazones, thiocarbazones, hydrazone carboxylates and carbonic acid hydrazones.

As used herein, an oxyamino group has the formula —O—NH$_2$. An oxime has the formula —O—N=R.

As used herein, a protected hydrazino or a protected oxyamino group refers to a hydrazino or oxyamino group that has been derivatized as a salt of the hydrazino or oxyamino group, including but not limited to, mineral acids salts, such as but not limited to hydrochlorides and sulfates, and salts of organic acids, such as but not limited to acetates, lactates, malates, tartrates, citrates, ascorbates, succinates, butyrates, valerates and fumarates; or with any amino or hydrazino protecting group known to those of skill in the art (see, e.g., Greene et al. (1999) *Protective Groups in Organic Synthesis* (3rd Ed.) (J. Wiley Sons, Inc.)). Preferred amino and hydrazino protecting groups herein include, but are not limited to, amino or hydrazino protecting groups useful in the synthesis of oligonucleotides, more preferably monomethoxytrityl (MMT), dimethoxytrityl (DMT), 9-fluorenylmethoxycarbonyl (FMOC), acetyl, trifluoroacetyl, benzoyl, or a hydrazone or oxime that is cleaved under mild acidic conditions (e.g., 100 mM acetate, pH 4.5–5.5) including, but not limited to, a hydrazone or oxime formed from a lower aliphatic aldehyde or ketone, preferably from acetone, propanal, cyclohexanone or 2-butanone.

As used herein surfaces including, but not limited to, plastics such as molded plastic or latex beads, modified or unmodified glass, metals such as gold or silver.

As used herein, an oligonucleotide is a nucleic acid, including, but not limited to, a ribonucleic acid (RNA), a deoxyribonucleic acid (DNA), and analogs thereof such as a protein nucleic acid (PNA), of any length, including chromosomes and genomic material, such as PCR products or sequencing reaction products, preferably DNA including double and single stranded forms. Single stranded forms of the oligonucleotides are also provided.

As used herein, a conjugate is a compound containing two components covalently linked together. For example, a first component, e.g., an oligonucleotide, is conjugated through a covalent hydrazone linkage to a second component, as defined herein, to form a conjugate.

As used herein, carbonyl derivatives include, but are not limited to, ketones and aldehydes.

As used herein, complementary reactive groups are those that, when reacted together, form a covalent linkage, including, but not limited to, a hydrazone or oxime linkage. Thus, a hydrazino group, as defined herein, is complementary to a carbonyl derivative. An oxyamino group is also complementary to a carbonyl derivative.

As used herein, "phosphorous based coupling group" refers to any phosphorous-containing group known to those of skill in the art to be useful in oligonucleotide synthesis including, but not limited to, phosphorodithioate, phosphorothioate, phosphoramidate, phosphonate, phosphodiester, phosphotriester, thiophosphoramidate, thionoalkylphosphonate, thionoalkylphosphotriester or boranophosphate. As is appreciated by those of skill in the art, a number of chemistries, including, but not limited to, phosphoramidite, phosphonamide, H-phosphonate and phosphotriester chemistries, have been developed for the stepwise solid phase synthesis of oligonucleotides (DNA or RNA) and modified analogs (i.e., 2' modified RNA, methylphosphonates, 3'–5' phosphoramidites, and phosophorothioates). All phosphorous based coupling groups known to those of skill in the art are contemplated for use in the reagents and methods provided herein. See, e.g., Glen Research Catalog of Products for DNA Research, Glen Reserach, Sterling, Va. Exemplary phosphorous based coupling groups herein include β-cyanoethyl-N,N-diisopropylphosphoramidites.

As used herein, a biopolymer is any compound found in nature, or derivatives thereof, made up of monomeric units. Biopolymers include, but are not limited to, oligonucleotides, peptides, peptide nucleic acids (PNAs), glycoproteins and oligosaccharides. Thus, the monomeric units include, but are not limited to, nucleotides, nucleosides, amino acids, PNA monomers, monosaccharides, and derivatives thereof.

As used herein, a macromolecule refers to a molecule of colloidal size (i.e., of high molecular weight), including, but not limited to, proteins, polynucleic acids, polysaccharides and carbohydrates.

As used herein, a reporter molecule refers to a molecule, such as an enzyme or indicator, which is capable of generating a detectable signal (e.g., by colorimetric, chemiluminescent, bioluminescent, fluorescent, or potentiometric means) when contacted with a suitable substrate under appropriate reaction conditions. Exemplary reporter enzymes include, but are not limited to, alkaline phosphatase, horseradish peroxidase, β-galactosidase, aryl esterase, sulfatase and urease.

As used herein, a nucleobase is a heterocyclic moiety that is found in naturally occurring oligonucleotides, including ribonucleic acids (RNA) and deoxyribonucleic acids (DNA), and analogs thereof, including deaza analogs. Preferred nucleobases include, but are not limited to, cytosines, uracils, adenines, guanines and thymines, and analogs thereof including deaza analogs.

As used herein, a fluorophore refers to a fluorescent compound. Fluorescence is a physical process in which light is emitted from the compound following absorption of radiation. Generally, the emitted light is of lower energy and longer wavelength than that absorbed. Preferred fluorophores herein are those whose fluorescence can be detected using standard techniques.

As used herein, a derivative of a compound includes a salt, ester, enol ether, enol ester, solvate or hydrate thereof that can be prepared by those of skill in this art using known methods for such derivatization. Salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Solvates and hydrates are complexes of a compound with one or more solvent or water molecule, preferably 1 to about 100, more preferably 1 to about 10, most preferably one to about 2, 3 or 4, solvent or water molecules.

It is to be understood that the compounds provided herein can contain chiral centers. Such chiral centers can be of either the (R) or (S) configuration, or can be a mixture thereof. Thus, the compounds provided herein may be enantiomerically pure, or be stereoisomeric or diastereomeric mixtures. In the case of amino acid residues, such residues may be of either the L- or D-form. The preferred configuration for naturally occurring amino acid residues is L.

As used herein, alkyl, alkenyl and alkynyl carbon chains, if not specified, contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 1 to 16 carbons preferably contain 1 to 5 double bonds. Alkynyl carbon chains of from 2 to 20 carbons preferably contain 1 to 8 triple bonds, and the alkynyl carbon chains of 2 to 16 carbons preferably contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-penytyl and isohexyl. The alkyl, alkenyl and alkynyl groups, unless otherwise specified, can be optionally substituted, with one or more groups, preferably alkyl group substituents that can be the same or different. As used herein, lower alkyl, lower alkenyl, and lower alkynyl refer to carbon chains having less than about 6 carbons. As used herein, "alk(en)(yn)yl" refers to an alkyl group containing at least one double bond and at least one triple bond.

As used herein, an "alkyl group substituent" includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 5 to 19 carbon atoms. Aryl groups include, but are not limited to groups, such as fluorenyl, substituted fluorenyl, phenyl, substituted phenyl, naphthyl and substituted naphthyl, in which the substituent is lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "cycloalkyl" refers to a saturated mono- or multicyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups can preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups can be composed of one ring or two or more rings which can be joined together in a fused, bridged or spiro-connected fashion, and can be optionally substituted with one or more alkyl group substituents. "Cycloalk(en)(yn)yl" refers to a cylcoalkyl group containing at least one double bond and at least one triple bond.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl can be optionally substituted with one or more, preferably 1 to 3, aryl group substituents. The heteroaryl group can be optionally fused to a benzene ring. Exemplary heteroaryl groups include, for example, furyl, imidazinyl, pyrrolidinyl, pyrimidinyl, tetrazolyl, thienyl, pyridyl, pyrrolyl, N-methylpyrrolyl, quinolinyl and isoquinolinyl, with pyridyl and quinolinyl being preferred.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle can be optionally substituted with one or more, preferably 1 to 3 aryl group substituents. Preferred substituents of the heterocyclic group include hydroxy, amino, alkoxy containing 1 to 4 carbon atoms, halo lower alkyl, including trihalomethyl, such as trifluoromethyl, and halogen. As used herein, the term heterocycle includes reference to heteroaryl.

As used herein, the nomenclature alkyl, alkoxy, carbonyl, etc. are used as is generally understood by those of skill in this art. For example, as used herein alkyl refers to saturated carbon chains that contain one or more carbons; the chains are straight or branched or include cyclic portions or be cyclic.

As used herein, alicyclic refers to aryl groups that are cyclic.

For purposes herein, where the number of any given substituent is not specified (e.g., "haloalkyl"), there can be one or more substituents present. For example, "haloalkyl" includes one or more of the same or different halogens. As another example, "$C_{1-3}$alkoxyphenyl" can include one or more of the same or different alkoxy groups containing one, two or three carbons.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to, cyanide, cyanate, thiocyanate, selenocyanate, trifluoromethoxy, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_3$—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O)NRR' in which R and R' are independently selected from aryl, preferably lower aryl, more preferably phenyl.

As used herein, "aralkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There can be optionally inserted along the alkylene group one or more oxygen, sulphur or substituted or unsubstituted nitrogen atoms, where the nitrogen substituent is alkyl as previously described. Exemplary alkylene groups include methylene (—$CH_2$—), ethylene (—$CH_2CH_2$—), propylene (—$(CH_2)_3$—), cyclohexylene (—$C_6H_{10}$—), methylenedioxy (—O—$CH_2$—O—) and ethylenedioxy (—O—$(CH_2)_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 2 to about 20 carbon atoms and at least one double bond, more preferably 1 to 12 carbons, even more preferably lower alkenylene. The alkenylene group is optionally substituted with one or more "alkyl group substituents." There can be optionally inserted along the alkenylene group one or more oxygen, sulphur or substituted or unsubstituted nitrogen atoms, where the nitrogen substituent is alkyl as previously described. Exemplary alkenylene groups include —CH=CH—CH=CH— and —CH=CH—$CH_2$—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, bivalent aliphatic hydrocarbon group, preferably having from 2 to about 20 carbon atoms and at least one triple bond, more preferably 1 to 12 carbons, even more preferably lower alkynylene. The alkynylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—$CH_2$—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "alk(en)(yn)ylene" refers to a straight, branched or cyclic, preferably straight or branched, bivalent aliphatic hydrocarbon group, preferably having from 2 to about 20 carbon atoms and at least one triple bond, and at least one double bond; more preferably 1 to 12 carbons, even more preferably lower alk(en)(yn)ylene. The alk(en)(yn)ylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alk(en)(yn)ylene groups include —C=C—$(CH_2)_n$—C≡C—, where n is 1 or 2. The term "lower alk(en)(yn)ylene" refers to alk(en)(yn)ylene groups having up to 6 carbons. Preferred alk(en)(yn)ylene groups are lower alk(en)(yn)ylene, with alk(en)(yn)ylene of 4 carbon atoms being particularly preferred.

As used herein, "arylene" refers to a monocyclic or polycyclic, preferably monocyclic, bivalent aromatic group, preferably having from 5 to about 20 carbon atoms and at least one aromatic ring, more preferably 5 to 12 carbons, even more preferably lower arylene. The arylene group is optionally substituted with one or more "alkyl group substituents." There can be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group are optionally substituted with one or more, preferably 1 to 3, aryl group substituents.

As used herein, "alkylidene" refers to a bivalent group, such as =CR'R", which is attached to one atom of another group, forming a double bond. Exemplary alkylidene groups are methylidene (=$CH_2$) and ethylidene (=$CHCH_3$). As used herein, "aralkylidene" refers to an alkylidene group in which either R' or R" is and aryl group.

As used herein, "amido" refers to the bivalent group —C(O)NH—. "Thioamido" refers to the bivalent group —C(S)NH—. "Oxyamido" refers to the bivalent group —OC(O)NH—. "Thiaamido" refers to the bivalent group —SC(O)NH—. "Dithiaamido" refers to the bivalent group —SC(S)NH—. "Ureido" refers to the bivalent group —HNC(O)NH—. "Thioureido" refers to the bivalent group —HNC(S)NH—.

As used herein, "semicarbazide" refers to —NHC(O)NHNH—. "Carbazate" refers to the bivalent group —OC(O)NHNH—. "Isothiocarbazate" refers to the bivalent group —SC(O)NHNH—. "Thiocarbazate" refers to the bivalent group —OC(S)NHNH—. "Sulfonylhydrazide" refers to the group —$SO_2$NHNH—. "Hydrazide" refers to the bivalent group —C(O)NHNH—. "Azo" refers to the bivalent group —N=N—. "Hydrazinyl" refers to the bivalent group —NH—NH—.

As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid.

As used herein, when any particular group, such as phenyl or pyridyl, is specified, this means that the group is unsubstituted or is substituted. Preferred substituents where not specified are halo, halo lower alkyl, and lower alkyl.

As used herein, a composition refers to any mixture of two or more products or compounds. It can be a solution, a suspension, liquid, powder, a paste, aqueous, non-aqueous or any combination thereof.

As used herein, a combination refers to any association between two or more items.

As used herein, fluid refers to any composition that can flow. Fluids thus encompass compositions that are in the form of semi-solids, pastes, solutions, aqueous mixtures, gels, lotions, creams and other such compositions.

As used herein, substantially identical to a product means sufficiently similar so that the property of interest is sufficiently unchanged so that the substantially identical product can be used in place of the product.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11, 942).

A. Functional Polymers and Functional Polymer/Biomolecule Conjugates and Immobilization to Surfaces.

Biomolecules incorporating a first reactive component and functional polymers incorporating a second reactive component that forms a covalent bond when reacted with first reactive component on the biomolecule are provided. Surfaces that are not modified but form electrostatic or hydrophobic interactions with polymer/biomolecule conjugates are provided as well as surfaces that are modified to incorporate the first reactive component or a reactive component of similar reactivity. In the case where the surface is modified with the first component the polymer/bioconjugate possesses available second components to form a covalent bond between the polymer and the surface (FIG. 1).

The preparation of the ternary system requires a covalent reaction scheme wherein the biomolecule/polymer/surface conjugate is mediated by electrophilic/nucleophilic/electrophilic or nucleophilic/electrophilic/nucleophilic covalent chemistries. In the example of an electrophilic/nucleophilic/electrophilic system the biomolecule is modified to incorporate a electrophile such as an aldehyde, the polymer is modified to incorporate a nucleophile that reacts with the electrophilic first component on the biomolecule, such as a hydrazine or aminooxy moiety and the surface is modified to incorporate an electrophile, such as an aldehyde, succinimidyl ester or isothiocyanante that reacts with the nucleophile incorporated on the surface. The electrophile on the surface may be the same or different as incorporated on the biomolecule. An overview of this method is described in the scheme below:

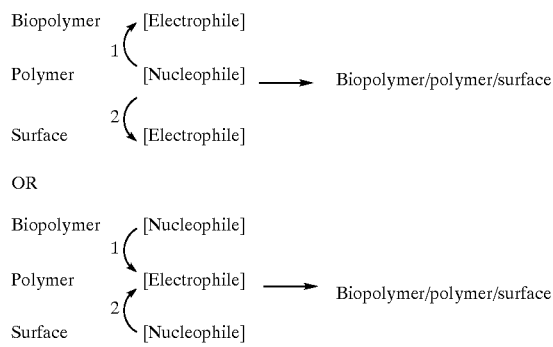

Reactivity overview of the prepartion of Ternary Biopolymer/Polymer/Surface System A most preferred enablement of this invention includes the use of a linking chemistry between all three components of the invention that incorporates moieties that are stable when incorporated on any of the three components and when required form covalent and/or electrostatic or other linkage rapidly and in most cases irreversibly. It is of utmost importance that any modification does not interfere with the biological properties of the biomolecule. There may be certain instance wherein reversibility of the linkage is important however.

It is an embodiment of the invention that the biomolecules are modified to incorporate a first reactive component of a bioconjugate couple. Bioconjugate couples include, but are not limited to maleimido/thiol, α-bromoacetamido/thiol, succinimidyl ester/amino, avidin/biotin, hydrazine/carbonyl and pyridyldisulfide/thiol. In a preferred embodiment the polymers are modified to possess a protected or unprotected hydrazino, a protected or unprotected oxyamino, or a carbonyl group for formation of a hydrazone or oxime linkage with an appropriately modified surface or biopolymer. The hydrazino moiety can be an aliphatic, aromatic or heteroaromatic hydrazine, semicarbazide, carbazide, hydrazide, thiosemicarbazide, thiocarbazide, carbonic acid dihydrazine or hydrazine carboxylate (see, FIG. 2). The protecting groups are salts of the hydrazino or oxyamino group, or any amino or hydrazino protecting groups known to those of skill in the art (see, e.g., Greene et al. (1999) *Protective Groups in Organic Synthesis* (3rd Ed.) (J. Wiley Sons, Inc.)). The carbonyl moiety can be any carbonyl-containing group capable of forming a hydrazone linkage with one or more of the above hydrazino moieties. Thus, in particularly preferred embodiments include 6-hydrazinonicotinamide moiety or 4-thiosemicarbazidobenzamide moiety. Preferred carbonyl moieties include aldehydes and ketones. Particularly preferred embodiments for irreversible linkages are hydrazones formed from aromatic ketones or aldehydes and aromatic hydrazines due to their increased stability or oximes formed from ketones and aminooxy moieties.

The design/selection of the polymer to be used in any specific application is dependent upon a variety of criteria. These criteria include the properties of the surface, the conditions of the protocols that the polymer will be exposed both before and after immobilization and to avoid deleterious interactions with the biomolecule. Therefore it is anticipated that cationic, anionic or neutral polymers may be used in this invention. Polymers may be prepared by modification of pre-synthesized polymers or reactive function or their protected forms may be incorporated on monomers prior to polymerization. Polymers may be homopolymers, copolymers or block co-polymers. Polymers made be composed on synthetic or natural polymers or any combination thereof. The specific application will dictate the desired properties of the polymer.

A preferred embodiment of the invention for immobilization on silica/glass surfaces includes cationic polymers derived from natural or unnatural polyaminoacids wherein one or more monomer possesses a cationic moiety such as amino or guanidinium groups. The monomers of natural polyaminoacids include lysine, ornithine or guanidine or any combination thereof. Cationic polymers prepared from non-natural sources include cationic groups including primary or secondary amines. A preferred synthetic cationic polymers includes but are not limited to polyethyleneimine. Polymers may be composed of a single monomer unit to form a homo-polymer or multiple monomers to form hetero-polymers tertiary amino or quaternary ammonium groups may also be included in the polymer to incorporate a cationic non-nucleophilic function. Preferred cationic polymers include poly-1-lysine and polyethyleneimine.

It is also anticipated for modification of silica surfaces that cationic polymers may be modified with reactive functionalities and subsequently coated on the surface. Current methods describe the immobilization of unmodified cationic polymers such as poly-1-lysine on glass slides for the electrostatic immobilization of polynucleotides. In a preferred embodiment of this invention amine-containing cationic polymers such as poly-1-lysine is modified with the first component of a bioconjugate couple and subsequently immobilized on the glass surface. In a most preferred embodiment poly-1-lysine is modified to possess hydrazine, aminooxy or carbonyl groups. The immobilized functionalized polymer is then reacted directly with a biomolecule possessing the second component of the bioconjugate couple for example carbonyl-containing biomolecule for covalent attachment to a hydrazine or aminooxy modified poly-1-lysine or a hydrazine or aminooxy modified biomolecule for covalent attachment to a carbonyl-modified poly-1-lysine. The most preferred hydrazine, aminooxy and carbonyl moieties are similar to those described below.

In another embodiment glass immobilized with functionalized cationic polymers can themselves react covalently as well as eletrostatically to anionic polymers possessing both the first component of a bioconjugate couple and covalently linked to biomolecules.

Polymers may be modified to possess any one component of a bioconjugate couple. Bioconjugate couples include, but are not limited to maleimido/thiol, a-bromoacetamido/thiol, succinimidyl ester/amino, avidin/biotin, hydrazine/carbonyl and pyridyldisulfide/thiol. In a preferred embodiment the polymers are modified to possess a protected or unprotected hydrazino, a protected or unprotected oxyamino, or a carbonyl group. for formation of a hydrazone or oxime linkage with an appropriately modified surface or biopolymer. The hydrazino moiety can be an aliphatic, aromatic or heteroaromatic hydrazine, semicarbazide, carbazide, hydrazide, thiosemicarbazide, thiocarazide, carbonic acid dihydrazine or hydrazine carboxylate (see, FIG. 1). The protecting groups are salts of the hydrazino or oxyamino group, or any amino or hydrazino protecting groups known to those of skill in the art (see, e.g., Greene et al. (1999) *Protective Groups in Organic Synthesis (3rd Ed.)* (J. Wiley Sons, Inc.)). The carbonyl moiety can be any carbonyl containing group capable of forming a hydrazone linkage with one or more of the above hydrazino moieties. Preferred carbonyl moieties include aldehydes and ketones.

It is an object of the invention that biomolecules conjugated to polymers include synthetic peptides, proteins, synthetic oligonucleotides, polynucleotides derived from natural sources or synthesized via enzyme-mediated reactions including polymerases and reverse transcriptases. Biomolecules also include carbohydrates and glycoproteins.

It is an object of this invention to use unmodified surfaces to immobilize the polymer/biomolecule conjugate via electrostatic and/or hydrophobic interaction. In a preferred embodiment with unmodified glass a cationic polymer/biomolecule conjugate is immobilized via electrostatic interaction between the cationic polymer and the unmodified glass.

It is a further embodiment of the invention to employ surfaces with reactive moieties to form a covalent linkage with the second reactive component incorporated on the polymer of the polymer/biomolecule couple. The component incorporated on the polymer is chosen from one component of a bioconjugate couple. Bioconjugate couples include, but are not limited to maleimido/thiol, a-bromoacetamido/thiol, succinimidyl ester/amino, avidin/biotin, hydrazine/carbonyl and pyridyldisulfide/thiol. In a preferred embodiment the polymers are modified to possess a protected or unprotected hydrazino, a protected or unprotected oxyamino, or a carbonyl group for formation of a hydrazone or oxime linkage with an appropriately modified surface or biopolymer. The hydrazino moiety can be an aliphatic, aromatic or heteroaromatic hydrazine, semicarbazide, carbazide, hydrazide, thiosemicarbazide, thiocarazide, carbonic acid dihydrazine or hydrazine carboxylate (see, FIG. 1). The protecting groups are salts of the hydrazino or oxyamino group, or any amino or hydrazino protecting groups known to those of skill in the art (see, e.g., Greene et al. (1999) *Protective Groups in Organic Synthesis (3rd Ed.)* (J. Wiley Sons, Inc.)). The carbonyl moiety can be any carbonyl-containing group capable of forming a hydrazone linkage with one or more of the above hydrazino moieties. Thus, in particularly preferred embodiments include 6-hydrazinonicotinamide moiety or 4-thiosemicarbazidobenzamide moiety. Preferred carbonyl moieties include aldehydes and ketones. A particularly preferred embodiment is aromatic ketones and aldehydes.

A. Oligo/polymer/surface Systems

It is an additional object of the present invention to provide ternary oligo/polymer/surface embodiments for genomic screening by hybridization. The use of such ternary systems provides more cost effective, reproducible microarrays than that currently produced. The use of these systems allows the immobilization of 5-150 mer oligonucleotides. This invention will allow direct capture of solid phase synthesized full length oligonucleotides from a crude cleaved oligonucleotide mixture as only the terminally functionalized oligonucleotide will form a covalent linkage with the polymer and the unmodified capped failure sequences will be washed away. Also the covalent linkage will be performed in solution unlike spotting techniques wherein a modified oligonucleotide is contacted with a modified surface and allowed to react in a solid/liquid two-phase system. This latter method is sub-optimal as very small volumes, pLs to ηLs of oligonucleotide, are used which dry quickly inefficient immobilization. The method of this invention is preferable over synthesis of oligonucleotide on the chip as failure sequences will not be immobilized and longer sequences>25 mers can be efficiently immobilized. The longer oligonucleotides are preferred for genetic expression analysis as differences in the melting temperature, Tm, between sequences is less variable leading to better results.

The most direct, simple and efficient preparation of an oligonucleotide/polymer conjugate would have the following properties: (1) direct incorporation of the first component of the bioconjugate couple directly on the oligonucleotide during solid phase synthesis without the requirement for any post-synthetic activation, (2) indefinite stability of both components of the bioconjugate couple following incorporation on either the oligonucleotide or the polymer, (3) good kinetics of covalent bond formation between the modified oligonucleotide and the modified polymer without the need for a reagent-mediated reaction or competing reactions on the bioconjugate couple moieties, (4) simple incorporation of the first component of the bioconjugate couple on the surface of choice, (5) fast kinetic of immobilization of the oligonucleotide/polymer conjugate on the modified surface, (6) long term stability of the oligonucleotide/polymer conjugate on the surface.

It is a specific object of the invention that the first reactive component of the bioconjugate couple is incorporated on the 3', 5' or an internal position of the oligonucleotide to be conjugated to the polymer. It is a most preferred embodiment that the first reactive component is incorporated on either the 3' or 5' end of the oligonucleotide. In a preferred embodiment the polymer is modified to possess a protected or unprotected hydrazino, a protected or unprotected oxyamino, or a carbonyl group for formation of a hydrazone or oxime linkage with an appropriately modified surface and/or biopolymer. The hydrazino moiety can be an aliphatic, aromatic or heteroaromatic hydrazine, semicarbazide, carbazide, hydrazide, thiosemicarbazide, thiocarazide, carbonic acid dihydrazine or hydrazine carboxylate (see, FIG. 3). The protecting groups are salts of the hydrazino or oxyamino group, or any amino or hydrazino protecting groups known to those of skill in the art (see, e.g., Greene et al. (1999) *Protective Groups in Organic Synthesis (3rd Ed.)* (J. Wiley Sons, Inc.)). The carbonyl moiety can be any carbonyl-containing group capable of forming a hydrazone linkage with one or more of the above hydrazino moieties. Thus, in a particularly preferred embodiment includes 6-hydrazinonicotinamide moiety or 4-thiosemicarbazidobenzamide moiety. Another preferred embodiment includes the use of carbonyl moieties, i.e. aldehydes and ketones. A particularly preferred embodiment is aromatic ketones and aldehydes.

Surfaces modified to possess the first reacting group of a bioconjugate couple are provided. In one embodiment glass surfaces can be modified to possess the first component of the bioconjugate couple by a treatment with a silane possessing the first component or a reactive component of similar reactivity. The first component can also be incorporated on a cationic polymer including but not limited to poly-1-lysine or polyethyleneimine and the modified polymer immobilized on the glass surface via electrostatic interactions. Silica-based surfaces such as glass, silica beads or fiber optic cables modified to possess aldehyde or hydrazine/aminoxy functionalities are preferred embodiments. Plastic, polystyrene (latex) surfaces modified to possess the first reactive group are further described. Either carbonyls or hydrazines as the first component of the hydrazine/carbonyl bioconjugate couple are preferred embodiments wherein the second component is incorporated on the polymer. Other surface similarly functionalized such as metals, including gold or silver, are further preferred embodiments.

B. Polynucleotide/polymer/surface

Polynucleotides may be functionalized in a several ways to possess first reactive component. It is mandatory that the functional group incorporated via modified triphosphates on the polynucleotide be stable to conditions used in the polymerase chain reaction or reverse transcriptase reaction. First components of bioconjugate couples that are suitable for this purpose include amino, hydrazine and carbonyl moieties. These functionalities are preferred embodiments of this invention.

In one enablement any of the three moieties may be incorporated at any position of a the base of a nucleoside triphosphate such that the modification does not interfere with both the incorporation of the triphosphate in the enzymic incorporation of the nucleoside in the growing polynucleotide and does not interfere with the hydrogen bonding properties of the synthesized polynucleotide. A variety of positions on all the natural nucleosides have been described including the 5-position of cytidine, thymidine and uridine. The N-4 position of thymidine and uridine has also been described. Functional moieties have also been incorporated on unnatural nucleosides such as deaza purines have been described and we anticipate that amino, hydrazine or carbonyl groups incorporated on these moieties would similarly function as described herein to produce desired conjugates when reacted with polymers possessing the second functionality.

In another embodiment one primer of the primer set is immobilized on a polymer and this multiple primer/polymer conjugate is combined with the second primer during polynucleotide synthesis. The PCR or reverse transcriptase product is immobilized on an unmodified or appropriately modified surface and subsequently heated to melt of the non-conjugated strand. One extremely important criterion is that the bond linking the primer to the polymer must be stable to the conditions required for elongation of the primers. Preferred embodiments include primers modified to possess a hydrazine or carbonyl moiety and the polymer is cationic and modified to possess a carbonyl or hydrazine moiety to react with its reaction partner respectively. If the product is to be immobilized via covalent and/or electrostatic interactions on a silica surface it is a preferred embodiment that the polymer be cationic. It may also be advantageous that the polymer be neutral and the reactive groups be neutral as the polynucleotide increases in length the charge of the conjugate will be increasingly negative and if a cationic polymer is used there is a possibility that the complex will be neutral and it may precipitate during elongation. Therefore a second preferred embodiment would employ a neutral polymer modified to incorporate either a hydrazine or carbonyl group that would react with a primer modified on the 5'-end with a carbonyl or hydrazine that would covalently link the oligonucleotide to the polymer via a hydrazone linkage. The hydrazone linkage is stable to elevated temperatures at physiological pH. It is a further embodiment that the linkage between the polymer and the oligonucleotide could be an amide bond formed by carbodiimide-mediated couple between amine and carboxyl groups either the polymer or the oligonucleotide.

A third method to immobilize a polynucleotide/polymer on a surface would be to incorporate on the 5'-end of a primer one or more first components and use this modified primer in a PCR or reverse transcriptase polynucleotide amplification reaction. Subsequently the product would be conjugated to a polymer that possesses the second reactive component that will form a covalent linkage to polynucleotide the first component. The polynucleotide/polymer would be immobilized on a surface and heated to melt the non-conjugated strand off the surface. It is extremely advantageous to remove the non-conjugated strand so it will not compete with the target during the hybridization step. Currently no methods are able to selectively immobilize only one strand. Preferred functional groups to be incorporated on the 5'-end on a primer include amines, hydrazines, oxyamines or aldehydes. To capture amine modified polynucleotides carbodiimide mediated amide formation to an carboxyl-containing polymer is anticipated. Other electrophilic surfaces such as epoxy, succinimidyl ester or isothiocyanates would similar react with the amino group. A preferred embodiment is to incorporate hydrazine or aminooxy groups on the primer and capture the reactive polynucleotide on a carbonyl containing polymer. Also incorporation of a carbonyl group on the primer followed by capture on a hydrazine or aminooxy containing polymer would form the desired polynucleotide/polymer conjugate. A cationic polymer incorporating the second component of the reaction is the preferred embodiment for immobilization on silica-based surfaces.

One can also envisage the incorporation of multiple first components on the 5'-end of the primer in dendrimeric or polymeric constructions. The use of multiple first components would increase the likelihood of covalent attachment to the polymer and the formation of multiple covalent attachments to the polymer. Cationic dendrimers themselves modified to incorporate multiple primers are a further embodiment of this invention. Preferred functionalities include those describe above for single first component modified primers.

C. Protein/polymer/surface

The production of "protein chips" for proteomic purposes is also anticipated using this invention.

The general process for immobilization of proteins or peptides as anticipated by this invention includes the following steps: (1) incorporation of a first reactive component on the protein or peptide, (2) incorporation of a second reactive component on a polymer that forms a covalent linkage with the first reactive component on the protein, (3) reacting the modified protein with the modified polymer to form a covalently linked protein/polymer conjugate, (5)

preparation of a modified or unmodified surface for immobilization of the protein/peptide conjuate and (5) contacting the peptide/polymer conjugate to unmodified or modified surface.

Examples of first and second reactive components include but are not limited to bioconjugate couples standardly used by one skilled in-the-art including maleimido/thiols, a-haloacetamides/thiol, amines/succinimidyl esters and hydrazine or aminooxy/carbonyl couples. It is extremely advantageous to use first and second components that have extended (>1 month) to indefinite stability following incorporation of the protein/peptide or polymer. Thus a preferred embodiment of this invention is the use of the hydrazine/carbonyl or aminooxy/carbonyl couples as incorporation of any of these moieties on protein/peptides have indefinite stability in neutral aqueous conditions.

Modification of the protein or peptide with carbonyl groups can be accomplished with carbonyl heterobifunctional succinimidyl esters including succinimidyl 4-formylbenzoate or succinimidyl 4-acetylbenzoate to incorporate aromatic carbonyl groups or succinimidyl levulinate to incorporate aliphatic ketone groups. It is well known to those skilled in the art that glycoproteins can be oxidized with sodium periodate to cleave 1,2-diol groups on carbohydrates to produce aldehydes. These oxidized glycoproteins are also suitably reactive for this purpose.

In a preferred embodiment proteins or peptides can be directly modified to incorporate hydrazine or hydrazide groups using the previously described bifunctional hydrazine, hydrazide or thiosemicarbazide reagents (as described in Schwartz et al., U.S. Pat. Nos. 5,753,520, 5,679,772, 5,420,285 and 5,206,370) including succinimidyl 6-hydraziniumnicot hydrochloride, succinimidyl 4-hydrazidiumbenzoate hydrochloride or succinimidyl 4-thiosemicarbazidium benzoate hydrochloride respectively.

The level of modification of either aldehyde or hydrazine groups can be controlled by controlling the stoichiometry of addition of the heterobifunctional reagents to the protein during the modification reaction. It is desirable to incorporate sufficient groups on the protein so that the kinetics of conjugation is appropriate and that overmodification does not compromise the biological function of the protein or lead to precipitation or other unwanted interactions of the protein.

Similar hydrazine or carbonyl containing polymers described above for the preparation of oligonucleotide/polymer conjugates are used to form conjugates with appropriately modified proteins or peptides. Addition of the carbonyl or hydrazine modified protein to the hydrazine or carbonyl modified polymer respectively leads to a covalently linked conjugate.

Surfaces described for immobilization of oligonucleotide/polymer conjugates can be used for immobilization of the above-described protein/polymer conjugates. In one preferred embodiment amino polymers including but not limited to poly-1-lysine or ornithine or polyethyleneimine are modified to incorporate hydrazine or carbonyl moieties and subsequently reacted with the appropriately modified proteins. The protein/polymer conjugate is then immobilize on glass surfaces that have been treated with aqueous ethanolic hydroxide solution followed by water washing and drying. The polycationic nature of the protein/polymer conjugate forms a stable electrostatic linkage. Alternately as described for the immobilization of the oligonucleotide/polymer conjugate the silica based surface can be modified to include the first component of the bioconjugate couple that will lead to both covalent and electrostatic linking of the polymer to the surface.

D. Peptide/polymer/surface Ternary System

Immobilization of synthetic peptides to surface via electrostatic interactions is not feasible due to varying charge and hydrophobic/hydrophilic nature of each peptide. Therefore it is an embodiment of this invention that one component of a bioconjugate couple is incorporated on the peptide either during solid phase synthesis or post-synthetically. The modified peptide is subsequently covalently linked to a polymer possessing the second component of the bioconjugate couple. The peptide/polymer conjugate is subsequently immobilized on a surface that possesses the first component of the bioconjugate couple that was incorporated on the peptide. In a most preferred embodiment of this enablement the hydrazine or aminooxy and carbonyl bioconjugate couple is employed. Carbonyl groups are incorporated on the C or N terminus of a peptide during solid phase synthesis using reagents such as succinimidyl 4-formylbenzoate or succinimidyl levulinate. Hydrazine groups are incorporated using appropriately protected forms of succinimidyl 6-hydrazinonicotinate.

The modified peptides are immobilized on the appropriately modified polymers to produce the peptide/polymer conjugate. The conjugate is subsequently immobilized on a surface containing the first component of the bioconjugate couple. In a most preferred embodiment a cationic polymer is immobilized on a glass surface possessing the first component.

EXAMPLES

Figure 4:
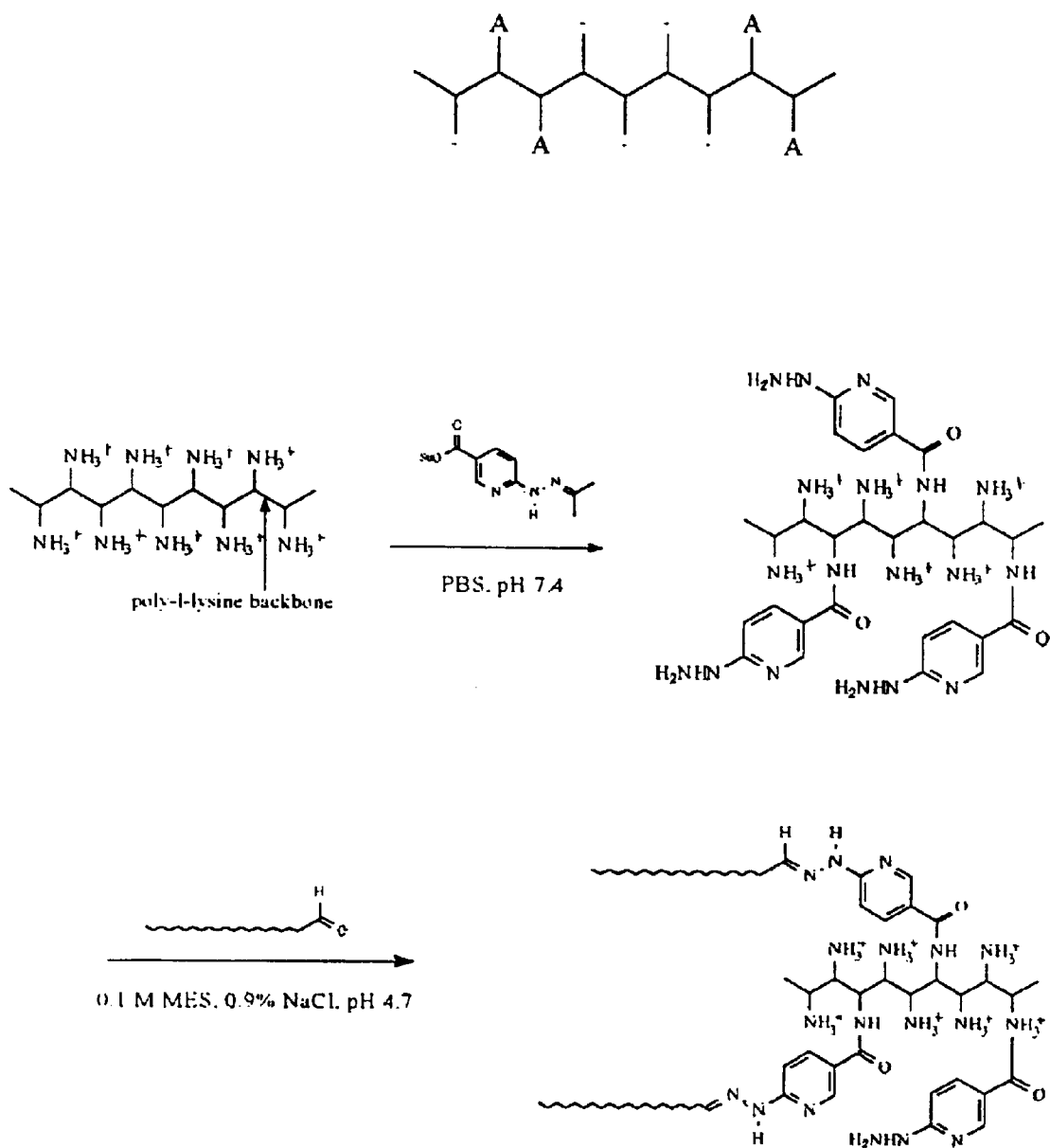
FIG. 4: Scheme used to prepare both HyNic-modified poly-l-lysine and conjugation to a 5'-aldehyde-modified oligonucleotide.

Example 1 (see FIG. 4)

Preparation of 5'-aldehyde modified oligonucleotides: 5'-aldehyde modified oligonucleotide 5'-OHC-aryl-TTT TTT TAG CCT AAC TGGA TGC CAT G-3' was obtained from Solulink, Inc (San Diego, CALIF.). The 5'-aldehyde was incorporated using Solulink's proprietary aldehyde phosphoramidite linker (Schwartz, filed Aug. 1, 2000

Preparation of HyNic::polyethyeleneimine: A solution of polyethyleneimine (50% by weight; 1 g; Sigma Chemicals, St. Louis, Mo.) in DI water (3 mL) was prepared and the pH lowered to 7.4 with concentrated hydrochloric acid (1.5 mL). 10× Conjugation buffer (1 M phosphate, 1.5 M NaCl, pH 7.4; 0.45 mL) was added. A solution of SANH (27.4 mg) was dissolved in DMF (200 uL). Four 1.0 mL aliquots were treated with SANH/DMF solution (0, 17.5, 35.0 and 52.5 uL) respectively. On addition the reaction mixtures became cloudy and were allowed to stand at room temperature for 2 hours. The reaction mixtures were centrifuged to remove any precipitate. Four NAP-25 columns (Apbiotech, Piscataway, N.J.) were pre-equilibrated with 0.1 M MES, 0.9% NaCl, pH 4.7. Fractions were analyzed by spotting 0.5 uL on a F490 silica gel TLC plate (Merck) and visualized using a short wavelength fluorescent lamp. UV positive fractions were combined and analyzed for hydrazine modification using a colorimetric assay by addition of an aliquot (2 uL) to a 0.5 mM solution of p-nitrobenzaldehyde in MES, pH 4.7 (98 uL) and recording A390 and quantifying using the molar extinction coefficient of the hydrazone formed (22000).

Preparation of HyNic::poly-1-lysine: A solution of poly-1-lysine (10 mg; Sigma Chemicals, St. Louis, Mo.; cat. #P-7890) was dissolved in conjugation buffer, 0.1 M phosphate, 0.15 M NaCl, pH 7.4 (1 mL). A solution of succinimidyl 6-hydrazinonicotinate acetone hydrazone (SANH; 1.3 mg) was dissolved in DMSO (13 uL). To two poly-1-lysine aliquots (200 uL) were added the SANH/DMSO solution (2.85 uL (10 equivalents) and 5.7 uL (20 equivalents)). The reaction mixtures were vortexed and incubated at room temperature for 2 h. The modified polymer was isolated by gel filtration on a NAP-25 column (Pharamacia) pre-equilibrated with 0.1 M MES, 0.9% NaCl, pH 4.7 buffer. Fractions (1 mL) were collected and analyzed by UV (A260). Fractions containing UV active product were combined to yield the desired product. The product was analyzed colorimetrically for hydrazine content by dissolving an aliquot (2 uL) in a 0.5 mM solution of p-nitrobenzaldehyde (98 uL) and incubating at 37° C. for 1 h.followed by taking A390 readings (extinction coefficient 22000). The HyNic:poly-1-lysine polymer was used directly in the conjugation step. The amine/hydrazine content was determined using the TNBSA assay (trinitrobenzenesulfonic acid; Pierce Chemical, Inc., Rockville, Ill.)

Preparation of oligonucleotide/HyNic:poly-1-lysine conjugate: In an initial preparation of oligonucleotide/polymer conjugates 5'-amino-oligonucleotide (2.6 uL of a 0.4715 OD/uL solution in water) was added to both unmodified poly-1-lysine (10 uL of a 5 mg/mL solution in PBS buffer) and to HyNic:poly-1-lysine (10 uL) solution in PBS buffer) containing 6M urea to a final volume of 200 uL) and the mixture was incubated at room temperature for 1 hour. After incubation an aliquot of each reaction mixture was diluted with PBS (95 uL) and their spectrum scanned (200–440 nm). Ultraviolet scans (200–400 nm) showed that the aldehyde oligonucleotide/HyNic:poly-1-lysine conjugate displayed an absorption at A360 indicating the formation of a HyNic/benzaldehyde hydrazone. The other combinations did not display any absorption other than oligonucleotide A260.

In a separate experiment both the amino and aldehyde modified oligonucleotides were reacted with the HyNic:poly-1-lysine polymer. Solutions of both amino and aldehyde oligos (0.1, 0.2, 0.4, 0.6, 0.8 and 1.0 ug/uL) were prepared in 0.1 M MES, 0.9% NaCl, pH 4.7 buffer. A solution of HyNic:poly-1-lysine (1 uL) in 8 uL 0.1 M MES, 0.9% NaCl, pH 4.7 buffer (80 uL) was prepared. An aliquot of each oligo concentration (1 uL) was added to the polymer solution (9 uL) and incubated at room temperature for 10 min.

Immobilization of oligonucleotide/polymer conjugate on various glass surfaces Aliquots of the oligonucleotide/HyNic:polymer solutions (0.3 uL) were spotted on unmodified glass surface, aminopropylsilane modified glass surface (Corning, Corning, N.Y.) and aldehyde modified glass surfaces (Cel Associates, Supplier: TeleChem (www.arrayit.com, Sunnyvale, Calif.) and allowed to dry. Following drying the plate was washed in 2×SSC, 0.01% SDS for 10 min and then allowed to dry.

Hybridization to immobilized oligonucleotide/polymer/surface system: The hybridization step was performed by preparing a solution of 5'-fluorescein labeled complementary oligonucleotide (sequence: 5'-FAM-CAT GGC ATC AGT TAG GCT-3'; 0.6 OD dissolved in 1.0 mL 2×SSC, 0.01% SDS and the solution was applied to the plate containing the immobilized oligo/polymer conjugate for 1 min. The plate was subsequently washed (2×SSC, 0.01% SDS) and dried. The plate was visualized initially by placing the slide on a long wavelength fluorescent lamp and obtaining a digital picture. The plate was also examined for fluorescence using a GSI Lumonics 5000 MicroArray Slide reader using fluorescein filters. Results indicated saturated signal down to 10 ng/uL and a signal within limits of detection at 5 ug/uL for the aldehyde modified oligonucleotide formulations. The amino modified oligonucleotides had very weak signals at all concentrations. Direct spotting of amino or aldehyde modified oligonucleotides on any surface gave no signal.

Titration of the 5'-OHC-oligo/polyK-HyNic conjugate: To test the minimal oligo (5'-TTT TTT TAG CCGT AAC TGA TGC CAT G-3') concentration conjugated to polyK-HyNic that will give a signal following hybridization to its fluorescently labeled complementary was performed. Decreasing concentrations (22, 11, 5.5, 2.3, 1.2, 0.6 and 0.0 uM) of both 5'-H2N-oligo and 5'-OHC-oligo were reacted with polyK/HyNic. Aliquots (0.3 uL) were spotted on unmodified glass, amino glass (Cel Sci) and aldehyde glass (Cel Sci) and allowed to dry. The plates were washed with 2×SSC (twice) and the hybridization was performed as above. Surfaces were visualized using a GSI Lumonics 5000 MicroArray reader.

Results indicate (1) no signal on 0.0 uM spot, (2) signals above the detection limit of the instrument were obtained down to 2.3 uM, (3) strong signals within the limits of the instrument were obtained at 1.2 and 0.6 uM and (4) there were equal signals on all three surfaces (5) the 5'-OHC-oligo/polyK-HyNic conjugate signals were much stronger than the weak 5'-H2N-oligo/polyK-HyNic signals and (6) direct spotting of both the amino and aldehyde oligos on any of the surfaces gave no signal.

The table below compares the efficiency of immobilization of the above method and current published methods. The immobilization step in this method is not reagent mediated unlike the Telechem method that requires a strong reducing reagent (sodium borohydride) for immobilization. Also this method does not require special controlled humidity conditions unlike the Mosaic method that requires a minimal humidity level to allow reaction to occur. Unlike the other methods this method results in multiple contact points, both covalent and electrostatic, to the surface and not a single point attachment.

|  | Spotting solution (uM) |
|---|---|
| this method | 0.6–1.3 |
| Telechem (www.arrayit.com) | 30 |
| Mosaic (www.mosaicbio.com) | 20 |

Demonstration of the Covalency of the Oligonuleotide/polymer Conjugate to the Aldehyde surface:

A 4×6 matrix experiment was designed comparing the oligonucleotide

5'-TTT TTT TAG CCGT AAC TGA TGC CAT G-3' with the following modifications:

1) 5'-H2N—
2) 5'-OHC—
3) 5'-H2NHN—
4) 5'-H2NHNCO— formulated with the following polymers at 2.5 uM oligo concentration:

1) polyK (poly-1-lysine (20K MW))
2) polyK/φCHO (10×)
3) polyK/φCHO (20×)
4) polyK/HyNic (100×)
5) polyK/HyNic (20×)
6) no polymer The oligonucleotide/polymer conjugates were prepared by incubating the appropriate concentration of oligonucleotide with the appropriate polymer (~0.03 uM poly-1;-lysine concentration); in 0.1 M MES, 0.9% NaCl, pH 4.7 for 30 min at room temperature to make a final 4 uM oligonucleotide solution.

0.3 uL aliquots of oligonucleotide/polymer conjugates were spotted on amino and aldehyde plates (Cel-Sci, Houston, Tex.). After drying the plates were washed with hybridization buffer (2×SSC, 0.1% SDS) at room temperature for 15 min by gentle shaking. After drying 5'-fluorescein-labelled complementary oligonucleotide (5'-FAM-CAT GGC ATC AGT TAG GCT-3') in (2×SSC, 0.1% SDS) was placed on the surface of the glass. Following a 1 minute incubation the plates were washed with hybridization buffer for 1 min and fluorescence was visualized under long wavelength UV light and a digital picture was taken.

The results (FIG. 5) were that only the 5'-OHC—oligo/polyK-HyNic at both modification levels on the aldehyde plates demonstrated fluorescence.

Example 2

SFB modification of poly-1-lysine: Two aliquots of poly-1-lysine (MW 20,700; Sigma Chemicals, St. Louis, Mo.; 200 uL of a 10 mg/mL solution in 100 mM phosphate, 150 mM NaCl, pH 4.7) were prepared. Succinimidyl 4-formylbenzoate (SFB; 1.75 mg; $7.1 \times 10^{-3}$ mmol) was dissolved in DMF (17.5 uL). Aliquots of the SFB/DMF solution (2.5 and 5.0 uL) were added to the poly-1-lysine solutions. The reaction mixtures were incubated at room temperature for 2 hours. The modified polymers were isolated by gel filtration using NAP-10 columns (APBiotech, Piscataway, N.J.) pre-equilibrated with 0.1 mM MES, 0.9% NaCl, pH 4.7. Fractions containing polymer were identified using the Bradford Protein Assay and combined. The amino content of the polymers was determined by TNBSA assay (trinitrobenzenesulfonic acid; Pierce Chemicals (Rockville, Ill.). The aldehyde content was determined using the 2-hydrazinopyridine assay as described in example 1 for the quantification of the aldehyde moiety on the oligonucleotide). The amine concentration was determined using the TNBSA assay described in Example 1. The modified polymers were used directly.

Preparation of 5'-hydrazine-modified oligonucleotide: A 25-mer phosphodiester oligonucleotide modified to incorporate a C6-aminolinker (Glen Research amino-C6 amidite ) was prepared (5'-NH2-(CH2)6-TTT TTT TAG CCT AAC TGGA TGC CAT G-3'; MW 7791 g/mol, 229.5 OD/umol; TriLink BioTechnologies, Inc., San Diego, Calif.). The oligonucleotide was dissolved in conjugation buffer (100 mM phosphate, 150 mM sodium chloride, pH 7.4) to a concentration of 0.92 OD/uL. To a solution of oligonucleotide (64 uL; 2 mg) was added DMF (32 uL). A solution of succinimidyl 4-hydrazinonicotinate acetone hydrazone (SANH; (3.8 mg) in DMF (100 uL) was prepared. An aliquot of the SANH/DMF solution (18.8 uL; 10 equivalents) was added to the oligonucleotide solution and the reaction allowed to incubate at room temperature overnight. The reaction was monitored by C18 RP-HPLC (solution A: 50 mM triethylammonium acetate, solution B: acetonitrile-gradient 0-50% A over 30 min; 50–80% over 10 min; 80–0% over 5 min). The hydrazine-modified oligonucletide was deprotected and purified using a Millipore 5K MWCO ultrafree diafiltration device by diluting the reaction mixture with 100 mM acetate, pH 4.7 and concentrating in the diafiltration device. The retentate was further washed with buffer (2×400 uL). The oligonucleotides was quantified by A260 assay and the hydrazine incorporation was determined using the p-nitrobenzaldehyde assay described in Example 1 and determined to be >95% hydrazine-modified.

Conjugation of hydrazine-modified oligonucleotide to aldehyde-modified poly-1-lysine: An aliquot of aldehyde-modified poly-1-lysine (~0.03 uM modified poly-1;-lysine concentration; 1 uL) was diluted with 0.1 M MES, 0.9% NaCl, pH 4.7 (8 uL) and an 1 uL aliquot of the prediluted oligonucleotide solutions was added and the reaction allowed to incubate at room temperature for 1 h. The solution was directly spotted on the glass.

Figure 6:
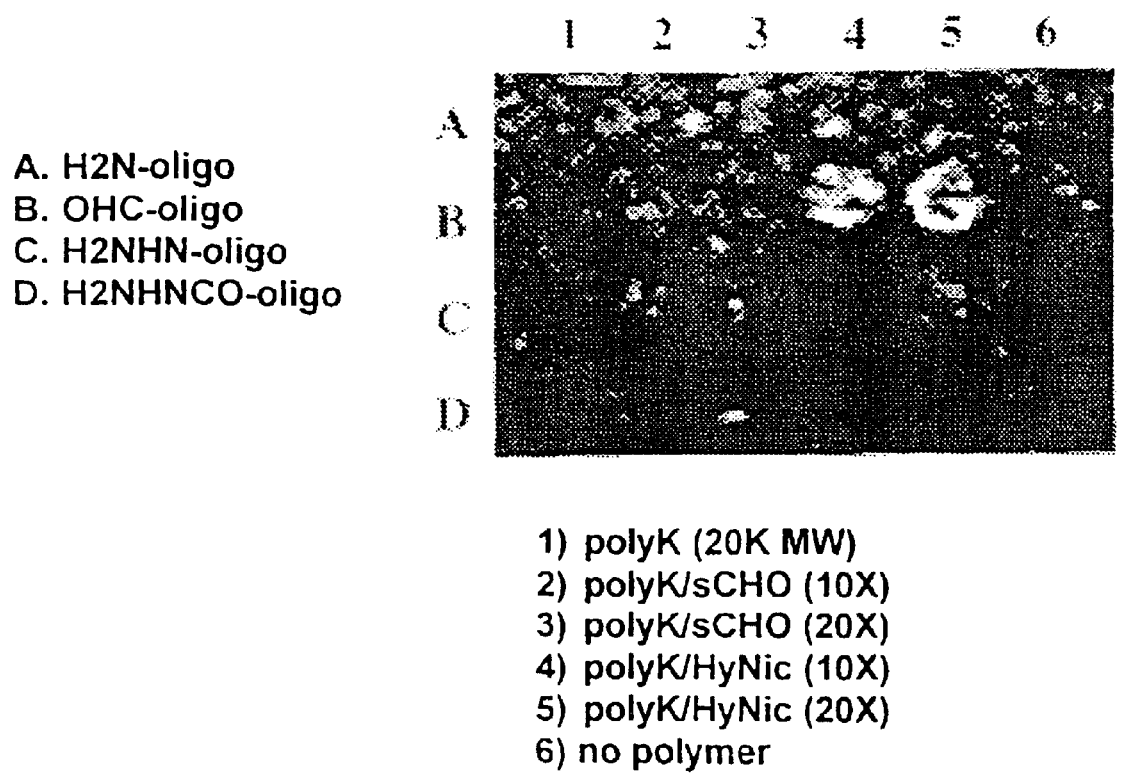
FIG. 6: Matrix experiment (see Example 2) demonstrating the covalent nature of the immobilization of a 5'-hydrazino oligo//SCHO/poly-l-lysine (polyK) conjugate on an amino modified glass slide following hybridization to its fluorescent complement.
Figure 7:
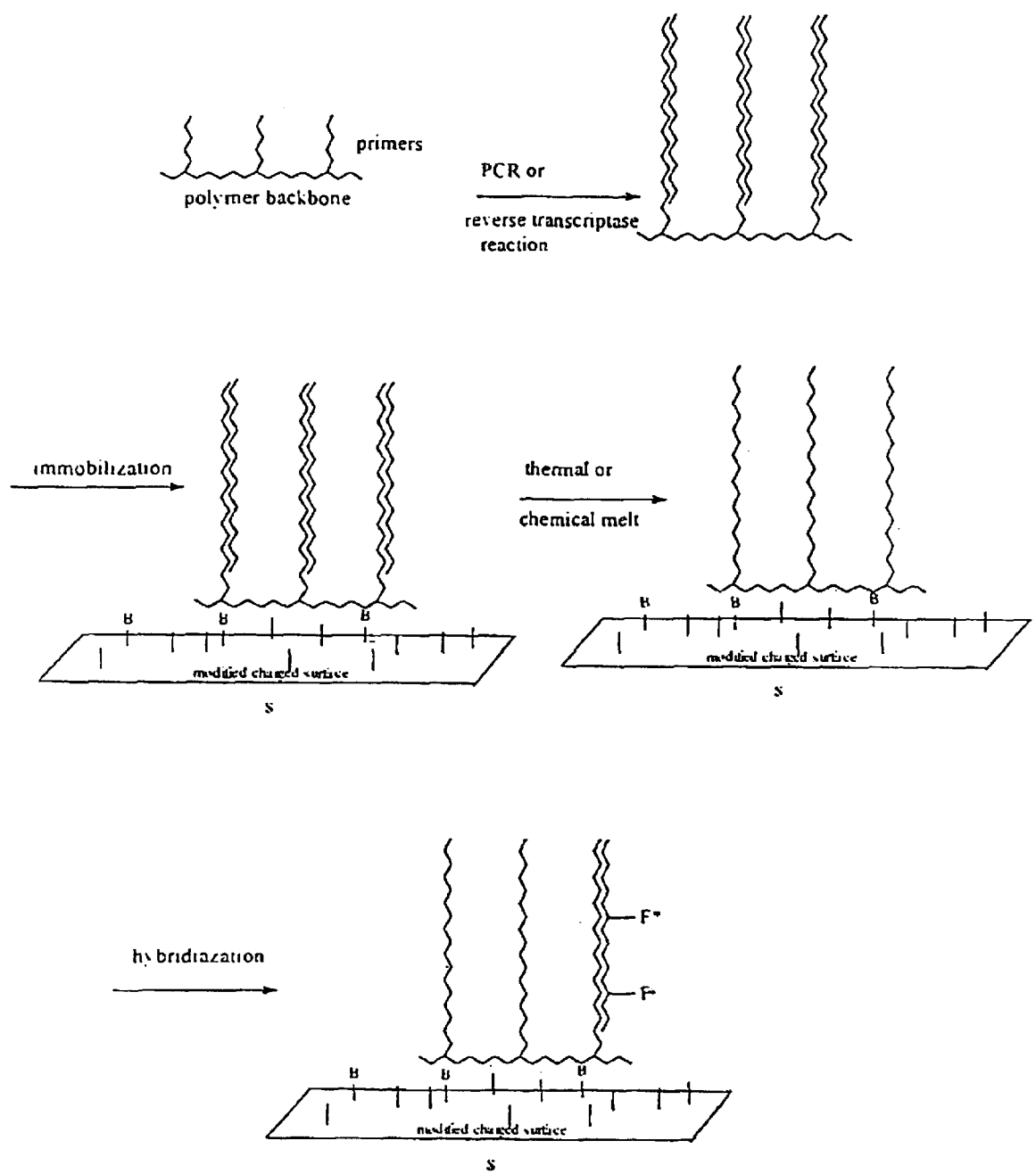
FIG. 7: Schematic demonstrating the steps in the preparation of a polynucleotide/polymer/surface system (see Example 7).

Hybridization to immobilized oligonucleotide/polymer/surface system was performed in an identical manner as described in Example 1. Both amino-glass and aldehyde glass were examined in a similar 4×6 matrix as described in Example 1. The results (FIG. 6) demonstrated only the 5'-H2NHN-oligo/polyK- φCHO at both modification levels on the amino plates demonstrated fluorescence and Example 3

Preparation of amino, aldehyde or hydrazine polynucleotides with appropriate triphosphates: Two primers and template DNA in reaction buffer containing a 70/30 mixture of dCTP and dCTP modified to incorporate a aromatic aldehyde group on the 5-position is added to dGTP, dTTP and dATP in equimolar amounts with heat stable DNA polymerase. A PCR reaction is performed by cycling of denaturation, annealing and extension steps. PCR products are purified using spincolumn [QIAGEN] to remove small molecule impurities.

Conjugation of PCR product to polymer The PCR product incorporating the aldehyde moiety is added to a solution of poly-1-lysine/HyNic polymer and incubated at room temperature for 4 h. The solution is used directly for immobilization.

Immobilization of polynucleotide/polymer to surface: Aliquots of the polynucleotide/polymer conjugate are spotted on aldehyde-modified glass surfaces and allowed to dry. The slide is washed with 2×SCC (three times).

Hybridization: The polynucleotide/polymer immobilized slide is used in a hybridization experiment with a fluorescently labeled cDNA sample.

Example 4

PCR of primer/polymer conjugate: The 5'-modified aldehyde primer/HyNic-polyK conjugate is prepared as in example 1 is combined with second primer and template DNA in reaction buffer containing dNTPs and heat stable DNA polymerase. A PCR reaction is performed by cycling of denaturation, annealing and extension steps. PCR products are purified using spincolumn [QIAGEN] to remove small molecule impurities.

Immobilization and hybridization of PCR/RT product: The polynucleotide/polymer conjugate is exchanged into 0.1 M MES, 0.9% NaCl, pH 4.7 and is spotted on aldehyde modified glass. The spot is allowed to dry and washed with 2×SSC. The second non-conjugated strand is removed by heat or urea treatment. The plate is hybridized to fluorescently labeled target and visualized in a MicroArray fluorescent instrument.

Example 5

PCR of 5'-aldehyde-modified primer: A 5'-modified aldehyde primer and the second non-modified primer are combined with template DNA in reaction buffer containing dNTPs and heat stable DNA polymerase. A PCR reaction is performed by cycling of denaturation, annealing and extension steps. PCR products are purified using spincolumn [QIAGEN] to remove small molecule impurities.

Conjugation of terminally labeled PCR product to HyNic/poly-1-lysine: The purified PCR product is added to a solution of HyNic/poly-1-lysine in 0.1 M MES, 0.9% NaCl, pH 4.7. The reaction is allowed to proceed at room temperature for 1–3 hours and the solution used directly. The slide is processed as described in Example 4 to melt off the second strand and subsequently hybridize to the immobilized strand.

Example 6

Preparation of aldehyde modified proteins: Anti-DNP polyclonal antibody (5 mg/mL in conjugation buffer (see Example 1)) is treated with a solution of succinimidyl 4-formyl benzoate in DMF (15 equiv). The reaction mixture is allowed to stand at room temperature for 3 h and the protein is isolated using a NAP 10 column pre-equilibrated with 0.1 M MES, 0.9% NaCl, pH 4.7). The protein containing fractions are combined and the protein concentration is determined using the BCA assay (Pierce Chemical, Rockville, Ill.) and the aldehyde concentration determined using the 2-hydrazinopyridine assay described in Example 2.

Conjugation of aldehyde modified proteins to hydrazine modified poly-1-lysine: An aliquot of the aldehyde-modified protein above is added to a solution of poly-1-lysine/HyNic and incubated at room temperature for 2 h. The solutions is used directly for spotting on the aldehyde surface.

Immobilization and antigen capture: A serial dilution of the protein/polymer conjugate is prepared and aliquots (1 nL) of the protein/polymer conjugate is spotted on aldehyde modified surfaces and allowed to dry. The surface is washed with conjugation buffer and challenged with the fluorescently modified antigen.

Example 7

Preparation of hydrazine modified proteins: In a similar manner to that described in Example 6 the protein is modified with succinimidyl 6-hydraziniumnicotinate hydrochloride (Schwartz et al., Bioconjugate Chem 2, 333 (1991)) to incorporate hydrazine groups on the protein. The hydrazine modified protein is subsequently conjugated to aldehyde modified poly-1-lysine (see Example 2). The protein/polymer conjugate is immobilized on an amino or hydrazine or oxyamino surface. The immobilized protein is similarly challenged with fluorescently labeled antigen as described in Example 6.

We claim:

1. A biomolecule/polymer conjugate wherein said biomolecule is conjugated to said polymer by a hydrazone bond, wherein said biomolecule is a protein, a glycoprotein or a peptide and wherein said polymer is a poly-L-lysine, poly-L-ornithine or polyethyleneimine.

2. A biomolecule/polymer conjugate wherein said biomolecule is conjugated to said polymer by a oxime bond, wherein said biomolecule is a protein, a glycoprotein or a peptide and wherein said polymer is a poly-L-lysine, poly-L-ornithine or polyethyleneimine.

* * * * *